US012778577B2

(12) United States Patent
Chase

(10) Patent No.: US 12,778,577 B2
(45) Date of Patent: Nov. 3, 2026

(54) SUTURING FORCEPS AND METHOD OF SUTURING

(71) Applicant: William Chase, Avon, CT (US)

(72) Inventor: William Chase, Avon, CT (US)

( * ) Notice: Subject to any disclaimer, the term of this patent is extended or adjusted under 35 U.S.C. 154(b) by 0 days.

(21) Appl. No.: 19/280,635

(22) Filed: Jul. 25, 2025

(65) Prior Publication Data

US 2026/0272448 A1 Sep. 17, 2026

Related U.S. Application Data

(62) Division of application No. 19/078,851, filed on Mar. 13, 2025, now Pat. No. 12,575,826.

(51) Int. Cl.

*A61B 17/04* (2006.01)
*A61B 17/062* (2006.01)
*A61B 17/29* (2006.01)

(52) U.S. Cl.

CPC ...... *A61B 17/0469* (2013.01); *A61B 17/0625* (2013.01); *A61B 17/2909* (2013.01); *A61B 2017/047* (2013.01)

(58) Field of Classification Search

CPC ............ A61B 17/0469; A61B 17/0625; A61B 17/064; A61B 17/2909; A61B 2017/047; A61B 17/0482; A61B 17/0483; A61B 17/0485; A61B 17/0491; A61B 2017/303

USPC .................................................. 606/144, 148

See application file for complete search history.

(56) References Cited

U.S. PATENT DOCUMENTS 4,596,249 A * 6/1986 Freda ................. A61B 17/0469 606/145
5,709,694 A * 1/1998 Greenberg ......... A61B 17/0483 606/147
5,728,112 A * 3/1998 Yoon ...................... A61B 17/04 606/139
5,797,927 A * 8/1998 Yoon .................. A61B 17/0469 606/139
5,843,100 A * 12/1998 Meade ................. A61B 17/062 606/147
6,146,392 A * 11/2000 Smith .................. A61B 17/062 606/147
6,984,237 B2 * 1/2006 Hatch ................ A61B 17/0469 606/144
8,272,300 B2 * 9/2012 Fournier ............ A61B 17/0483 606/205
9,861,355 B2 * 1/2018 Bourque ............ A61B 17/0469

(Continued)

*Primary Examiner* — Ahmed M Farah

(74) *Attorney, Agent, or Firm* — McCormick, Paulding & Huber PLLC

(57) ABSTRACT

Suturing forceps and method of suturing includes first and second tool arms being connected and configured to rotate about a pivot. First and second grip ends are arranged at respective distal ends of the first and second tool arms. A suture arm is connected to the first tool arm and/or the second tool arm through a differential rotation mechanism, such as a gear set or mechanism. The suture arm is configured to retain a suture needle. The differential rotation mechanism is configured such that rotation of the first tool arm and/or the second tool arm causes the differential rotation mechanism to cause the suture arm to rotate. A return arm is connected to the first tool arm and/or the second tool arm and the differential rotation mechanism is configured to cause the suture arm to rotate and disengage a suture needle from the suture arm.

8 Claims, 13 Drawing Sheets

(56) References Cited

U.S. PATENT DOCUMENTS

| | | | |
|---|---|---|---|
| 9,936,943 | B1 | 4/2018 | Mancini et al. |
| 2003/0220658 | A1 | 11/2003 | Hatch et al. |
| 2007/0100376 | A1 | 5/2007 | Mikkaichi et al. |
| 2011/0196387 | A1 | 8/2011 | Pantages et al. |
| 2017/0276989 | A1* | 9/2017 | Lin ..................... G02F 1/13338 |
| 2022/0015758 | A1* | 1/2022 | Dubrovsky ........ A61B 17/0469 |

* cited by examiner

SUTURING FORCEPS AND METHOD OF SUTURING

CROSS-REFERENCE TO RELATED APPLICATION

This application is a divisional of U.S. patent application Ser. No. 19/078,851, filed on Mar. 13, 2025, which is incorporated herein by reference in its entirety.

TECHNICAL FIELD

The present disclosure generally relates to methods and tools for installing sutures in animal or human tissue.

BACKGROUND

Forceps, hemostats and similar grasping/clamping tools are used to grasp small objects, when two or more objects need to be held simultaneously and/or when the hands are needed to perform another task. Such tools are often used to control bleeding during surgery. The terms forceps, hemostats and clamps are used interchangeably.

Forceps are typically structurally similar to pliers and scissors in the sense that a handle end (proximal end) and a tool end (distal end) have a pivot therebetween along the length of the tool, often at or near a midpoint thereof. Mechanically, forceps employ the principle of the lever to grasp and apply pressure. The pivot permits two arms of the forceps to be manipulated using handles to exert a clamping or grasping force at the tool end of the forceps. For example, the forceps may be used to clamp a blood vessel shut.

Suturing of body tissue can be a time-consuming aspect of a surgical procedure. In the past, surgical procedures often required a large access opening to expose the area requiring surgical repair. More recently, endoscopic and arthroscopic procedures have been used to allow the viewing of certain areas inside the body through a small puncture wound without exposing the entire body cavity. Endoscopes are used in conjunction with specialized surgical instrumentation to repair areas inside the body without having to cause large openings in the patient during surgery. Part of advances in endoscopic surgery include suturing methods and tools used to approximate, ligate and fixate tissues as part of the surgery. One challenge for such traditional devices and methods is that they presume ample room for the surgeon to manipulate the suture needle, suture thread and tools for placement of same.

SUMMARY

The present disclosure advantageously provides suturing forceps for installing one or more sutures in a target tissue in a quick, easy and consistent manner. In some embodiments, the suturing forceps include a first tool arm connected to a second tool arm, each configured to rotate about a pivot. A first grip end is arranged at a distal end of the first tool arm and a second grip end is arranged at a distal end of the second tool arm. A suture arm is connected to the first tool arm and/or the second tool arm through a differential rotation mechanism. The suture arm includes a needle holder configured to retain a suture needle. The differential rotation mechanism is configured such that rotation of the first tool arm and/or the second tool arm causes the differential rotation mechanism to cause the suture arm to rotate to insert a suture needle through target tissue, thereby installing a suture stitch.

In some embodiments, the suturing forceps includes a first tool arm connected to a second tool arm, each configured to rotate about a pivot. A first grip end is arranged at a distal end of the first tool arm and a second grip end arranged at a distal end of the second tool arm. A suture arm connected to the first tool arm and/or the second tool arm. A return arm is connected to the first tool arm and/or the second tool arm. The suture arm includes a needle holder configured to retain a suture needle. The return arm includes a needle catch configured to disengage the suture needle from the needle holder and retain the suture needle when the suture arm and the return arm are in a closed position after the suture arm has inserted the suture needle through target tissue, thereby installing a suture stitch.

Objects, features and advantages of the present invention will become apparent in light of the description of embodiments and features thereof, as illustrated by the accompanying figures.

DETAILED DESCRIPTION

Figure 1:
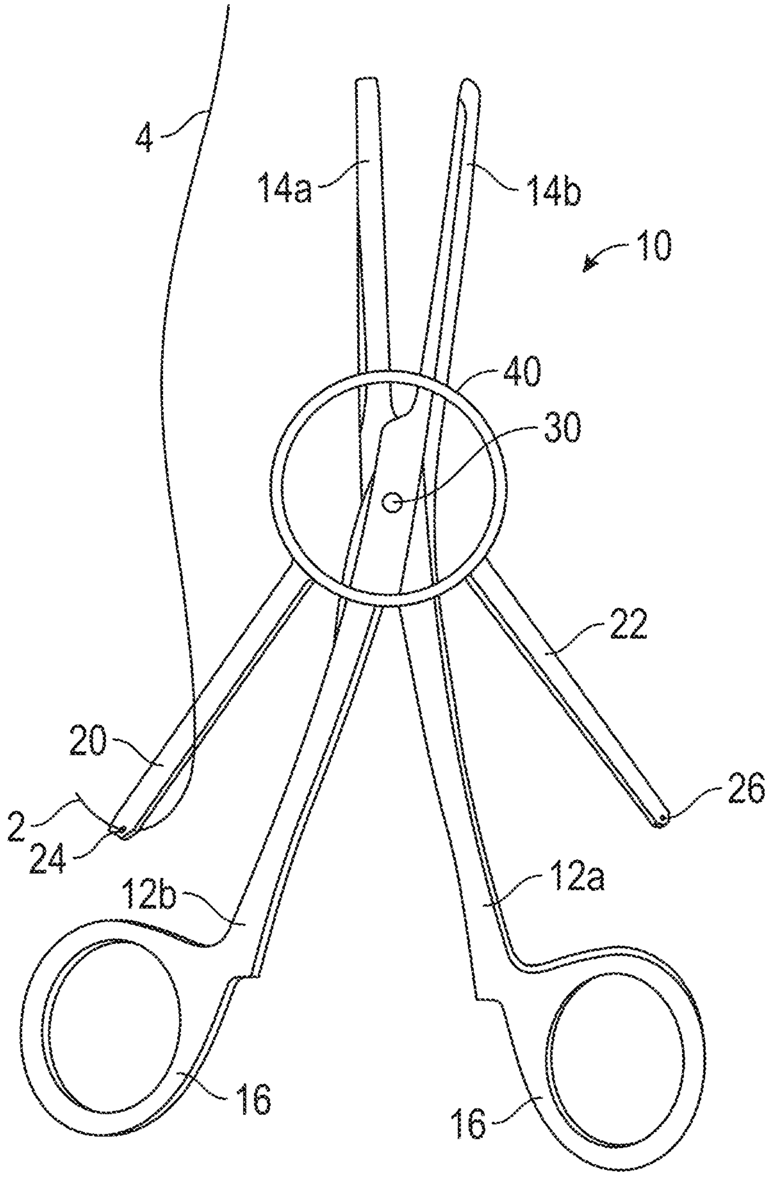
FIG. 1 is a top view of suturing forceps with a suture arm and return arm in an open position and with a suture needle retained by the suture arm in accordance with the present disclosure.

Referring to FIG. 1, suturing forceps 10 are shown in accordance with the present disclosure. The suturing forceps

10 include a pair of elongated arms, a first tool arm 12*a* and a second tool arm 12*b*. The tool arms 12*a*, 12*b* are pivotally connected at a pivot 30 at an intermediate point of each of the tool arms 12*a*, 12*b* so that the tool arms 12*a*, 12*b* can rotated about the pivot 30. In some embodiments, the tool arms 12*a*, 12*b* are connected by a pin at the pivot 30 to accomplish the pivot connection. Finger rings 16 are arranged at a handle end of each respective tool arm 12*a*, 12*b*, the handle end being a proximal end. The finger rings 16 are sized and shaped to be engageable by a thumb and finger of a hand of a user to cause rotation of the tool arms 12*a*, 12*b* about the pivot 30. Grip ends 14*a*, 14*b* are arranged at a tool end of each respective tool arm 12*a*, 12*b*, and are on the opposite side of pivot 30 from the handle ends. The grip ends 14*a*, 14*b* of the tool arms 12*a*, 12*b* are rotatable about the pivot 30 such that the grip ends 14*a*, 14*b* can be moveable toward and away from each other when a user manipulates the forceps 10 by engaging the finger rings 16 at the handle ends, squeezing the finger rings 16 together to accomplish movement of the grip ends 14*a*, 14*b* toward each other and pulling away the finger rings 16 from each other to move the grip ends 14*a*, 14*b* away from each other.

The grip ends 14*a*, 14*b* can be configured such that when brought together, the grip ends 14*a*, 14*b* grasp and/or clamp tissue located between the grip ends 14*a*, 1*b* with sufficient force such that the tissue cannot shift or slip from the grip ends 14*a*, 14*b*. The grip ends 14*a*, 14*b* are configured to grasp and/or clamp target tissue to be sutured. In some embodiments, additional tools, such as clamps, forceps or other devices, may be used in conjunction with the suturing forceps 10 to further fix tissue in place or otherwise render target tissue ready for suturing.

Figure 2:
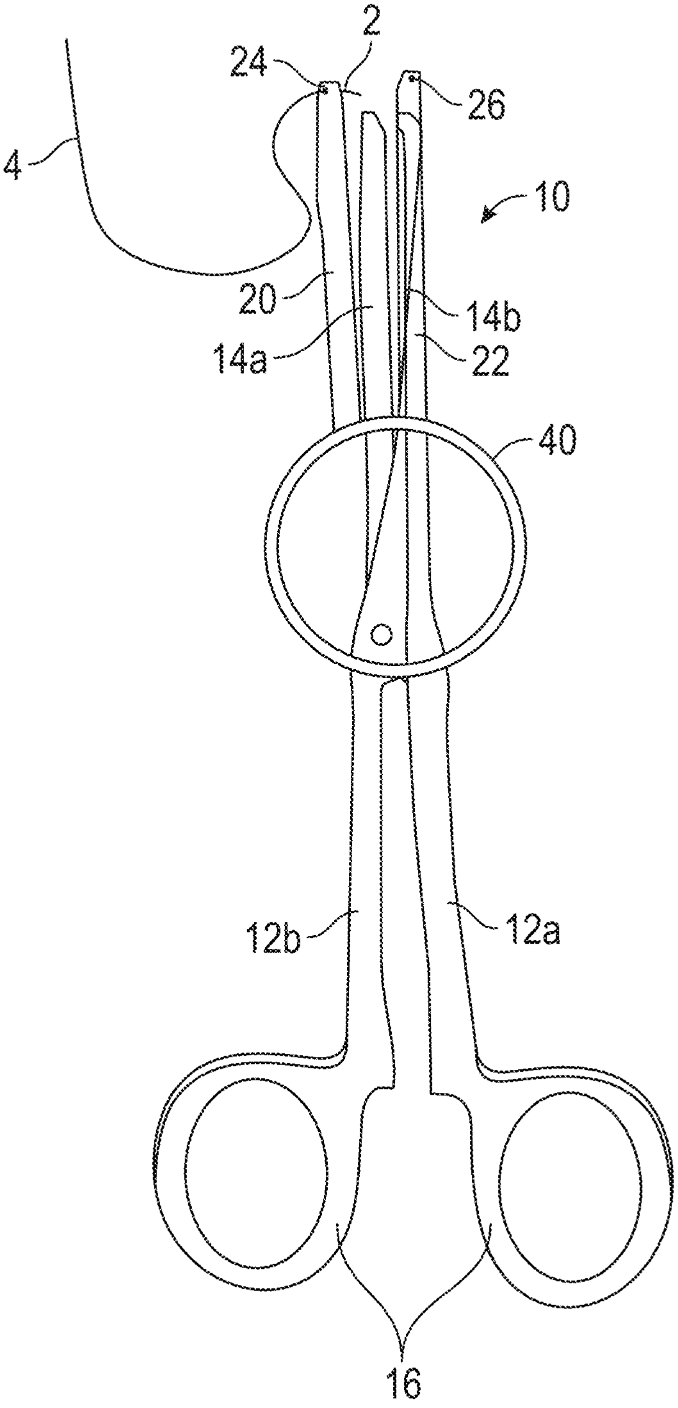
FIG. 2 is a top view of the suturing forceps of FIG. 1 with the suture arm and return arm in a closed position in accordance with the present disclosure.
Figure 3:
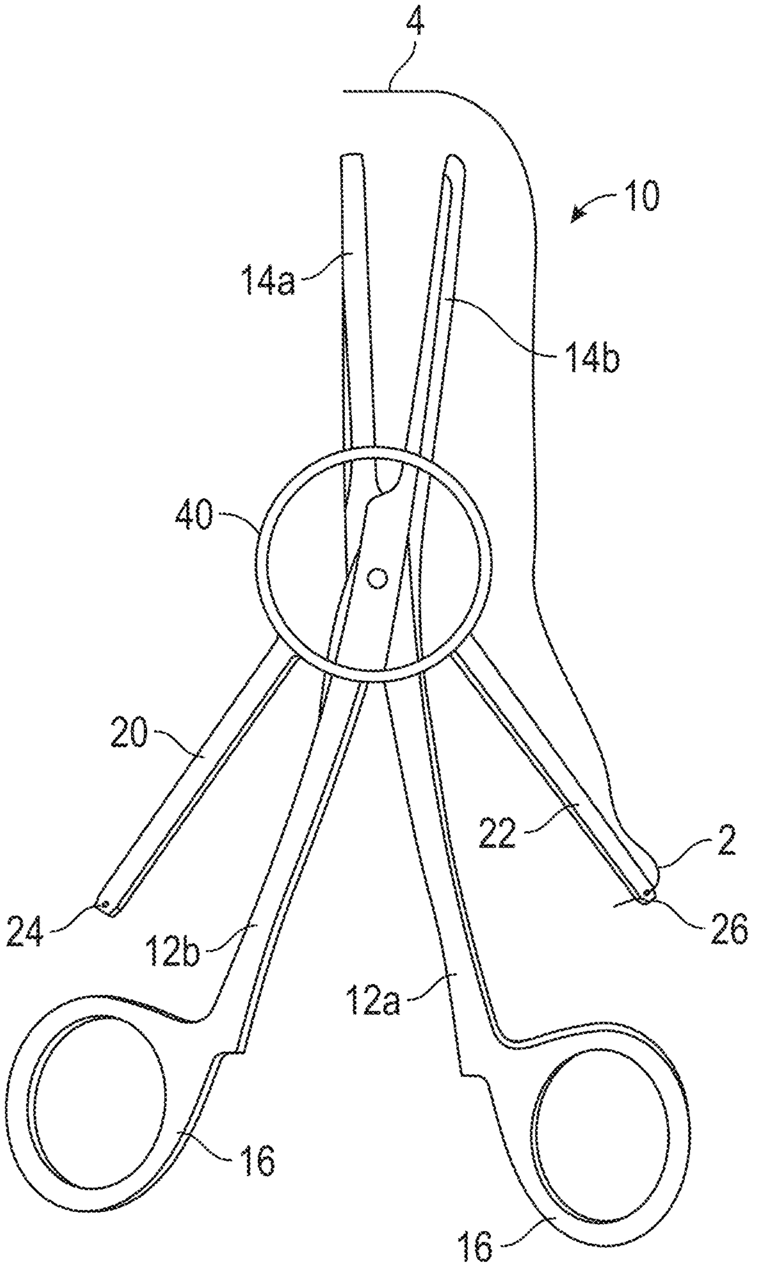
FIG. 3 is a top view of the suturing forceps of FIG. 1 with the suture arm and the return arm returned to the open position and with the suture needle retained by the return arm in accordance with the present disclosure.

A differential rotation mechanism 40 is connected to the tool arms 12*a*, 12*b* at or near the pivot 30. The differential rotation mechanism 40 in the embodiment shown in FIGS. 1-3 is a gear mechanism 40 (e.g. a gear set). The gear mechanism 40 transmits rotational movement to a suture arm 20 and a return arm 22, the suture arm 20 and return arm 22 being attached to different portions of the gear set 40. The gear mechanism 40 is attached to the tool arms 12*a*, 12*b* in such a way that the relative movement of the tool arms 12*a*, 12*b* caused by the user manipulating the handle ends at the finger rings 16 causes the transmission of mechanical movement or force to the gear mechanism 40. The gear mechanism 40 transforms this manipulation of the tool arms 12*a*, 12*b* into rotational movement of the suture arm 20 and return arm 22, in relatively opposite directions; e.g. the suture arm 20 being rotated clockwise and the return arm 22 being rotated counter-clockwise when moving the grip ends 14*a*, 14*b* toward each other (from the point of view of FIG. 1) and the suture arm 20 being rotated counter-clockwise and the return arm 22 being rotated clockwise when moving the grip ends 14*a*, 14*b* away from each other (from the point of view of FIG. 1).

The gear mechanism 40 is configured to deliver a differential in the rotational degree of movement of the suture arm 20 and return arm 22 in comparison to the rotational degree of movement of the grip ends 14*a*, 14*b*. For example, the user may manipulate such that a grip end 14*a*, 14*b* rotates through a rotational degree of 30° whereas the gear mechanism ratio is configured such that the suture arm 20 and/or the return arm 22 rotates through a rotational degree of 150°. As such, the gear mechanism is configure to permit a smaller rotational degree of the grip ends 14*a*, 14*b* in comparison to the suture arm 20 and return arm 22.

In FIG. 1, the suture arm 20 and return arm 22 are shown in an open state, where the grip ends 14*a*, 14*b* are in a non-clamping state. In FIG. 2, the suture arm 20 and return arm 22 are shown in a closed state, where the grip ends 14*a*, 14*b* are in a clamping state. In a clamping state, the grip ends 14*a*, 14*b* are positioned relatively closer to each other than the position of the grip ends 14*a*, 14*b* in the non-clamping state. The grip ends 14*a*, 14*b* do not necessarily touch one another in the clamping state, but tissue arranged between the grip ends 14*a*, 14*b* when in the clamping state would be clamped by the suturing forceps 10. While FIG. 2 shows that the suture arm 20 and return arm 22 are arranged approximately parallel with the tool arms 12*a*, 12*b* when in the closed state, it is within the scope of the present disclosure for there to be angles formed by the suture arm 20 and return arm 22 such that the suture arm 20 and return arm 22 to not be approximately parallel to the tool arms 12*a*, 12*b*.

The suture arm 20 includes a needle holder 24, which may be an opening defined by the suture arm 20 that is configured to retain a suture needle 2, or the needle holder 24 may be a distinct structural element connected to the suture arm 20 that is configured to retain the suture needle 2. The needle holder 24 is configured to retain the suture needle 2 with sufficient retention force such that the suture needle 2 is inserted into and passes through tissue arranged between the grip ends 14*a*, 14*b* when the suture arm 20 is moved from the open state shown in FIG. 1 to the closed state shown in FIG. 2. The needle holder 24 is shown at a distal end of the suture arm 20 from the gear mechanism 40, however, in some embodiments the needle holder 24 is at some intermediate point along the suture arm 20.

The return arm 22 includes a needle catch 26, which may be an opening defined by the return arm 22 that is configured to retain the suture needle 2 after the suture arm 20 has forced the suture needle 2 through the tissue arranged between the grip ends 14*a*, 14*b*, or the needle catch 26 may be a distinct structural element connected to the return arm 22 that is configured to retain the suture needle 2. The needle catch 26 is configured to retain the suture needle 2 with sufficient force to disengage or remove the suture needle 2 from the needle holder 24 when the return arm 22 is moved from the closed state shown in FIG. 2 to an open position shown in FIG. 3 when the user pulls the proximal ends (the handle ends) of the tool arms 12*a*, 12*b* away from each other with the finger rings 16. This movement of the handle ends toward the position shown in FIG. 3 results in the suture needle 2 disengaging from needle holder 24 and now resting with the return arm 22. Thus, the needle holder 24 does not retain the suture needle 2 while the suture arm 20 moves from the closed position (FIG. 2) to an open position (FIG. 3). The operation of the suture forceps 10 from the position shown in FIG. 1, to the position shown in FIG. 2 and then to the position shown in FIG. 3 causes a single suture stitch of suture thread 4 connected to the suture needle 2 to be installed in tissue held by the grip ends 14*a*, 14*b*.

When a user continues to move the handle ends of the tool arms 12*a*, 12*b* away from each other from the position shown in FIG. 3, the return arm 22 will bring the suture needle 2 into contact with the needle holder 24 of the suture arm 20. The needle holder 24 is configured to retain the suture needle 2 with sufficient force to disengage the suture needle 2 from the needle catch 26 of the return arm 22. The suturing forceps 10 are then brought back to the same position as shown in FIG. 1 with the difference being that one suture stitch with the suture thread 4 has been installed in the tissue of the human or animal. This process may be repeated as many times as desired by the user until the target tissue has the desired number of suture stitches.

The user can terminate the suturing process by cutting the suture thread 4 after the desired number of suture stitches are installed in the tissue and provide a suture thread termination knot or other end point termination as is known in the art or later developed.

Figure 4:
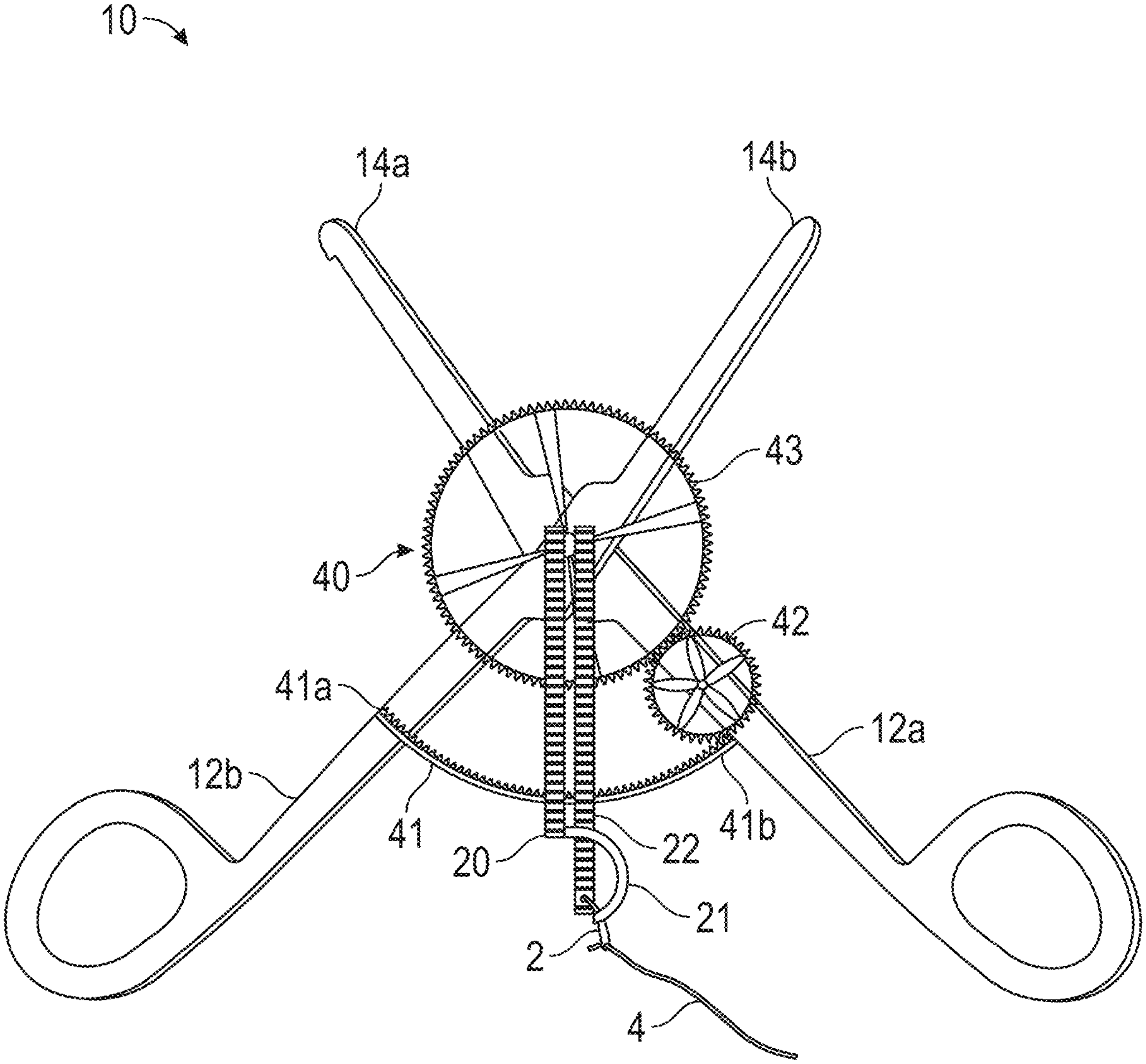
FIG. 4 is a top view of a suturing forceps with an exemplary gear mechanism in accordance with the present disclosure.

A person of ordinary skill in the art would readily understand that there are many different ways to effectuate the gear mechanism 40 to achieve the functions and results described above. Referring to FIG. 4, a suturing forceps 10 having an exemplary gear mechanism 40 is shown. The gear mechanism 40 includes a first toothed gear 41 fixedly connected to one tool arm 12*b* at one end 41*a* of the first toothed gear 41, while the other end 41*b* of the first toothed gear 41 is free floating. The teeth of the first toothed gear 41 are arranged to mesh and engage with a rotatable second toothed gear 42 fixedly connected to the other tool arm 12*a*. The second toothed gear 42 is arranged to mesh and engage with a third toothed gear 43. The third toothed gear 43 is arranged such that, through rotation of the third toothed gear 43, the third toothed gear 43 actuates the suture arm 20 and return arm 22 to perform the movements and functions described above.

In some embodiments, the gear mechanism 40 of the suturing forceps 10 of FIG. 4 could be mirrored on the back of the forceps 10 such that one gear is dedicated for actuating the suture arm 20 and a different gear is dedicated for actuating the return arm 22. It should be readily understood that the desired mechanical transfer of power could be accomplished many different ways without departing from the scope and spirit of the present disclosure. In some embodiments, a rack and pinion gear may be used instead of two rotary gears, etc.

In some embodiments, instead of the suture arm 20 and return arm 22 being configured with a needle holder 24 and needle catch 26, respectively, for effectuating the suturing and transfer of the suture needle 2, the suture arm 20 and/or the return arm 22 can be configured with rollers that accomplish the same functions as outlined above. For example and without limitation, rollers on the return arm 22 would move to push the needle 2 into rollers in the suture arm 20. The rollers would push the needle 2 through the flesh and into the rollers of the return arm 22. For transferring of the needle 2 in a similar manner as outlined above in connection with the needle holder 24 and needle catch 26 embodiment. The rollers would be fixed for all other segments. In some embodiments, the rollers may be a consumable item, which may allow for easier and efficient disinfecting of the suturing forceps 10. For example, the rollers could be removed and then the remaining elements of the suturing forceps 10 could be sterilized according to known methods (e.g. heated, UV-light applied, and/or chemical application). New rollers could be applied for use with the next patient. The rollers are moved from the action of the main rotational gearing. The rollers could be, for example, cylinders, that function to move the needle 2 through and reposition the needle 2 on the other side of the tissue once through. The rollers make the action repeatable such that the device can be rapidly opened and closed and moved slightly each cycle to form a uniform stitch.

In some embodiments, the distal end of the suture arm 20 and/or the return arm 22 are configured with two spring-loaded pads (grippers) with a high-friction surface (e.g. rubber) to hold the suture needle 2 in place. Other holding surfaces are within the scope of the present disclosure, such as metal with a roughened surface. The pads or grippers alternate to grip or release the suture needle depending on the position the arm 20, 22 is in (similar to clockwork gearing) or there would be an extension on the arm 20, 22 that would be linked to the gear mechanism 40 (could be a cam so the motion is dependent on the physical spot on the ring). When the arm 20 reaches the furthest point the extension, the gripper would push the needle 2 through the flesh and into the return 22 arm pads (pushing through the two pads of the gripper. Then at the starting position, the return arm 22 extension would swing forward to push the needle 2 back to the holder on the suture arm 20.

In some embodiments, such as the embodiment shown in FIG. 4, the suture arm 20 is shorter than the return arm 22 and has a suture arm extension 21 that is curved and is movable such that the extension 21 varies its rotational position depending on the position of the suture arm 20. In the shown embodiment, the suture arm extension 21 is magnetic and configured to retain the needle 2 with magnetic force. In addition or as an alternative to the magnet, the extension 21 may have grippers as discussed above that open/loosen depending on position of the suture arm 20 in order to facilitate transfer and movement of the needle 2.

Figure 5A:
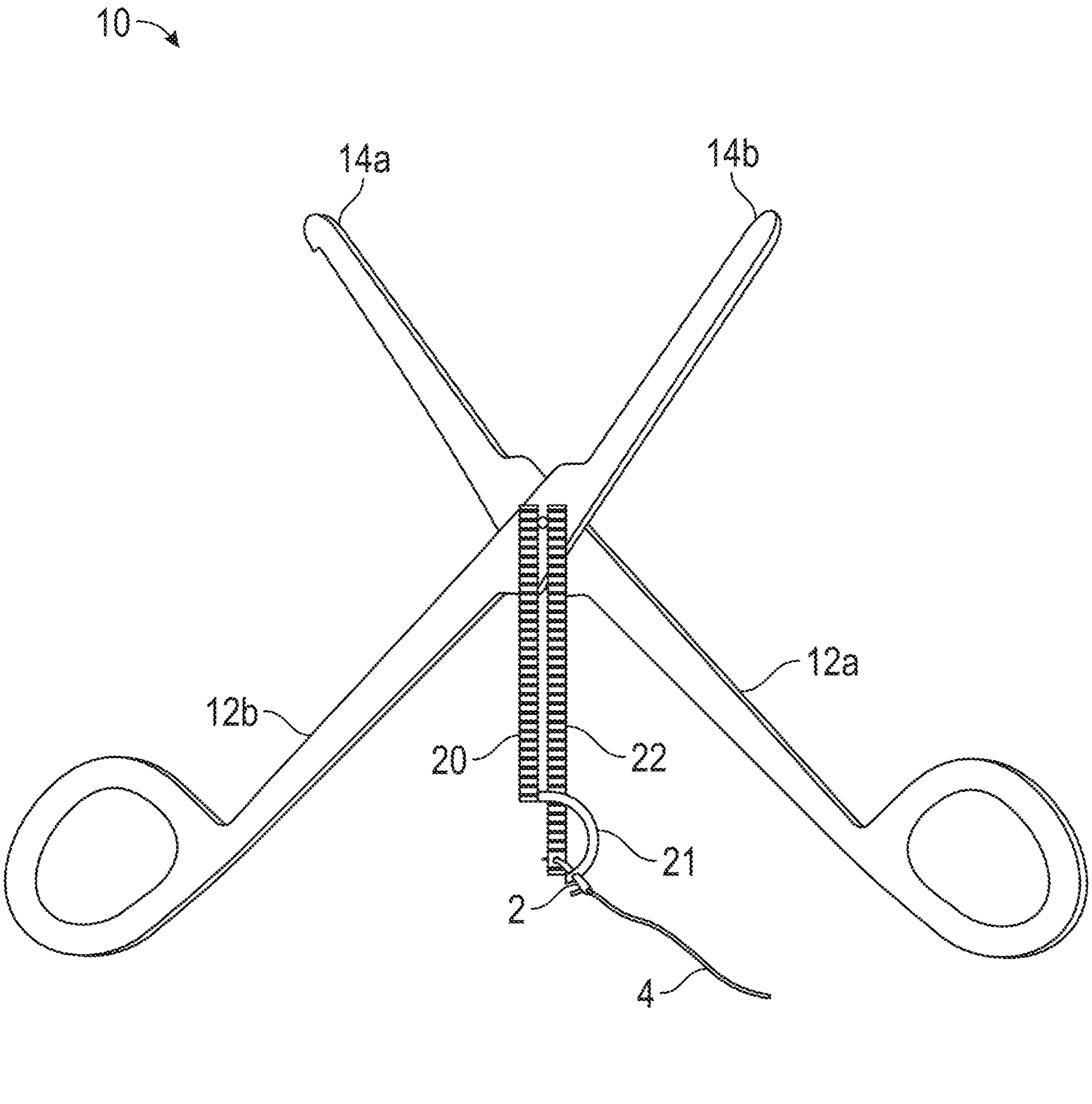
FIG. 5A is a top view of a suturing forceps with a movable suture arm extension at a starting position in accordance with the present disclosure.
Figure 5B:
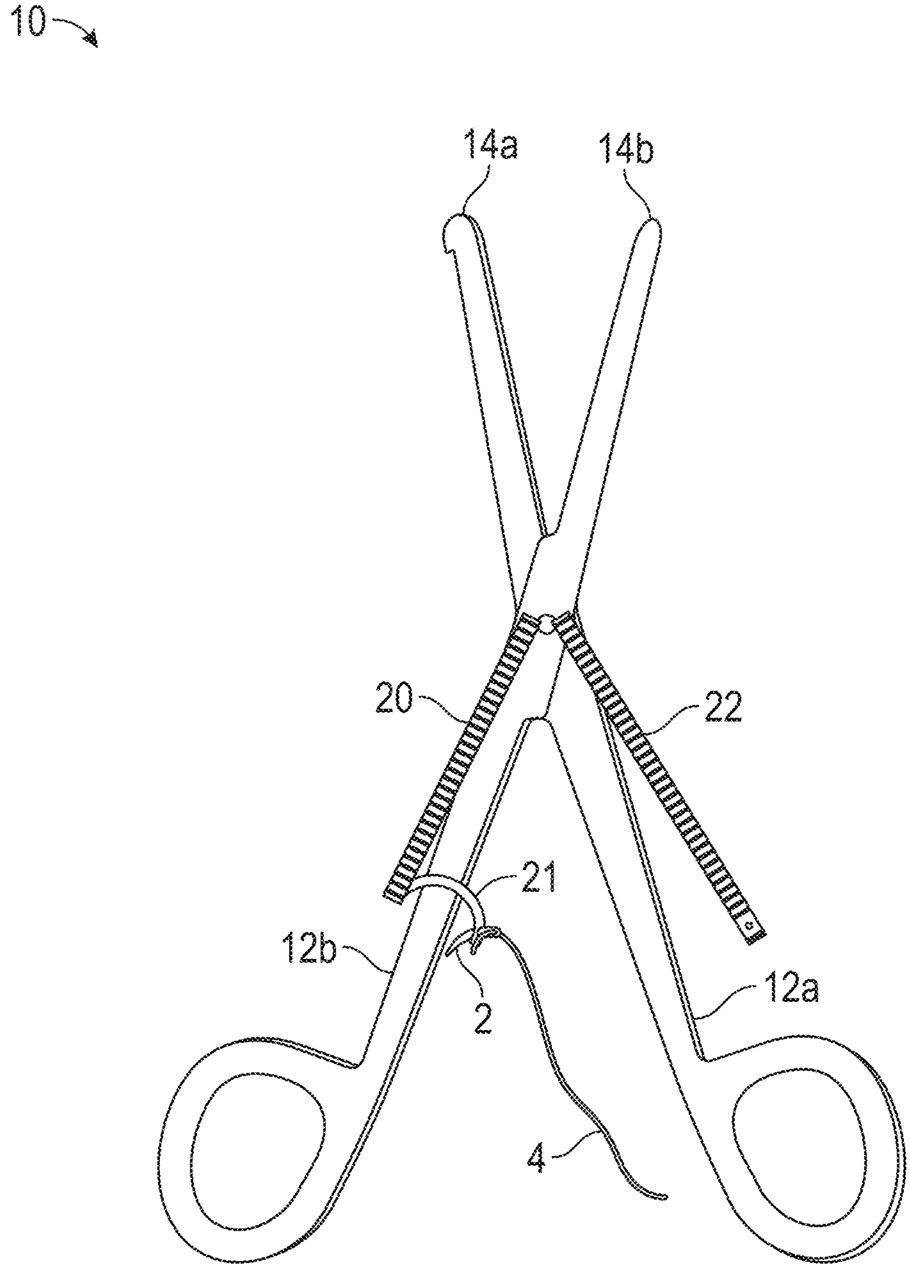
FIG. 5B is a top view of the suturing forceps of FIG. 5A in a different position in accordance with the present disclosure.
Figure 5C:
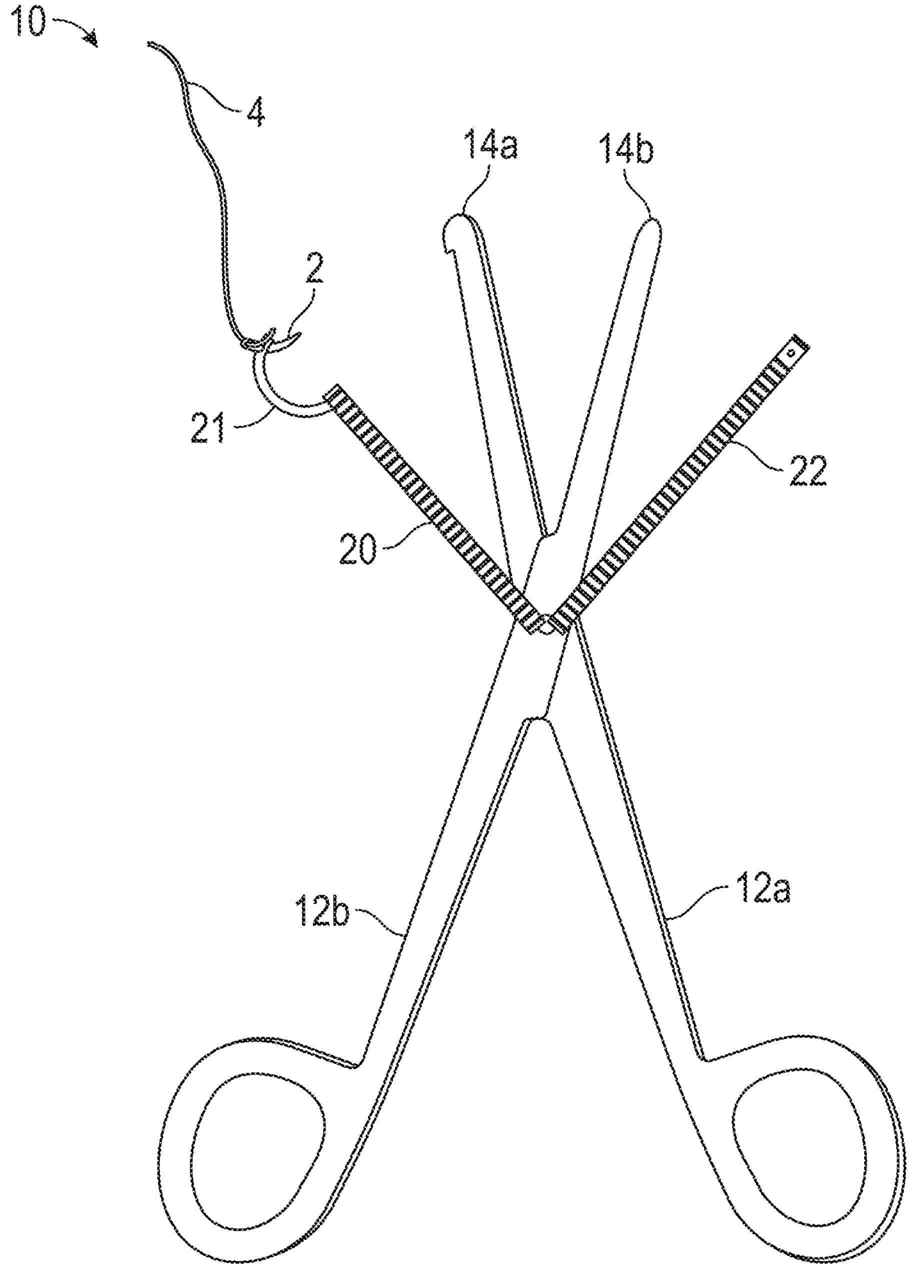
FIG. 5C is a top view of the suturing forceps of FIG. 5A in a different position in accordance with the present disclosure.
Figure 5D:
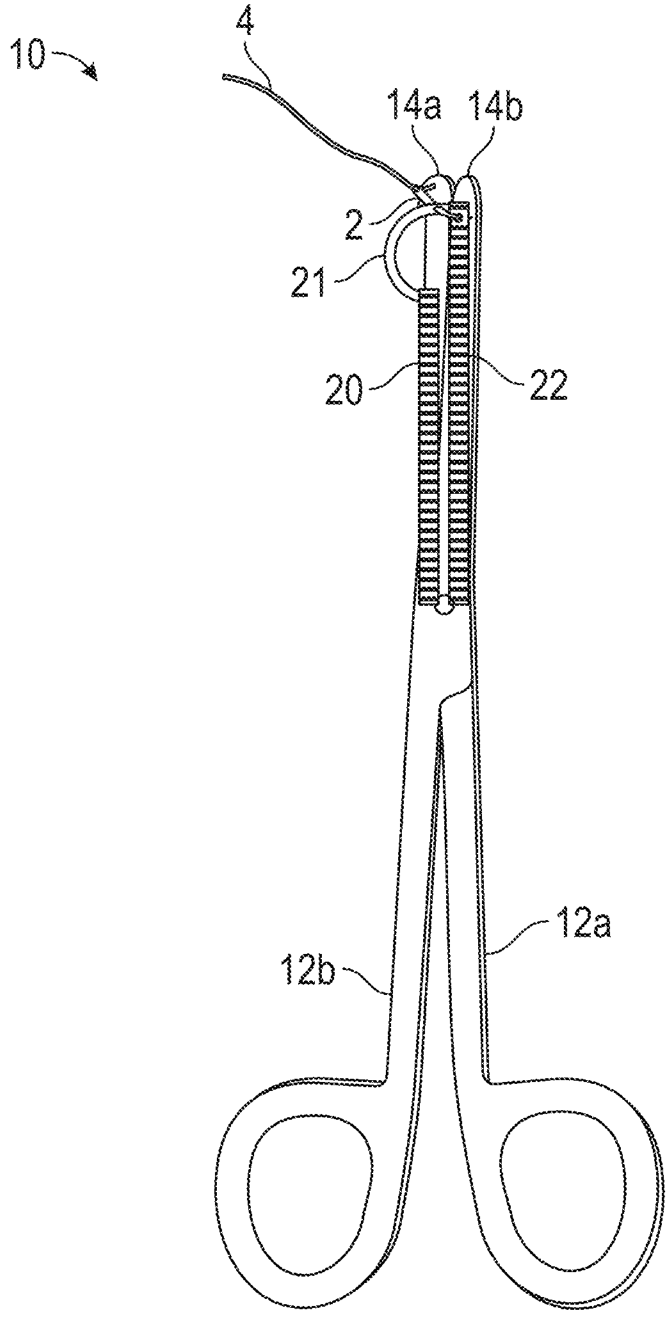
FIG. 5D is a top view of the suturing forceps of FIG. 5A in a different position in accordance with the present disclosure.
Figure 5E:
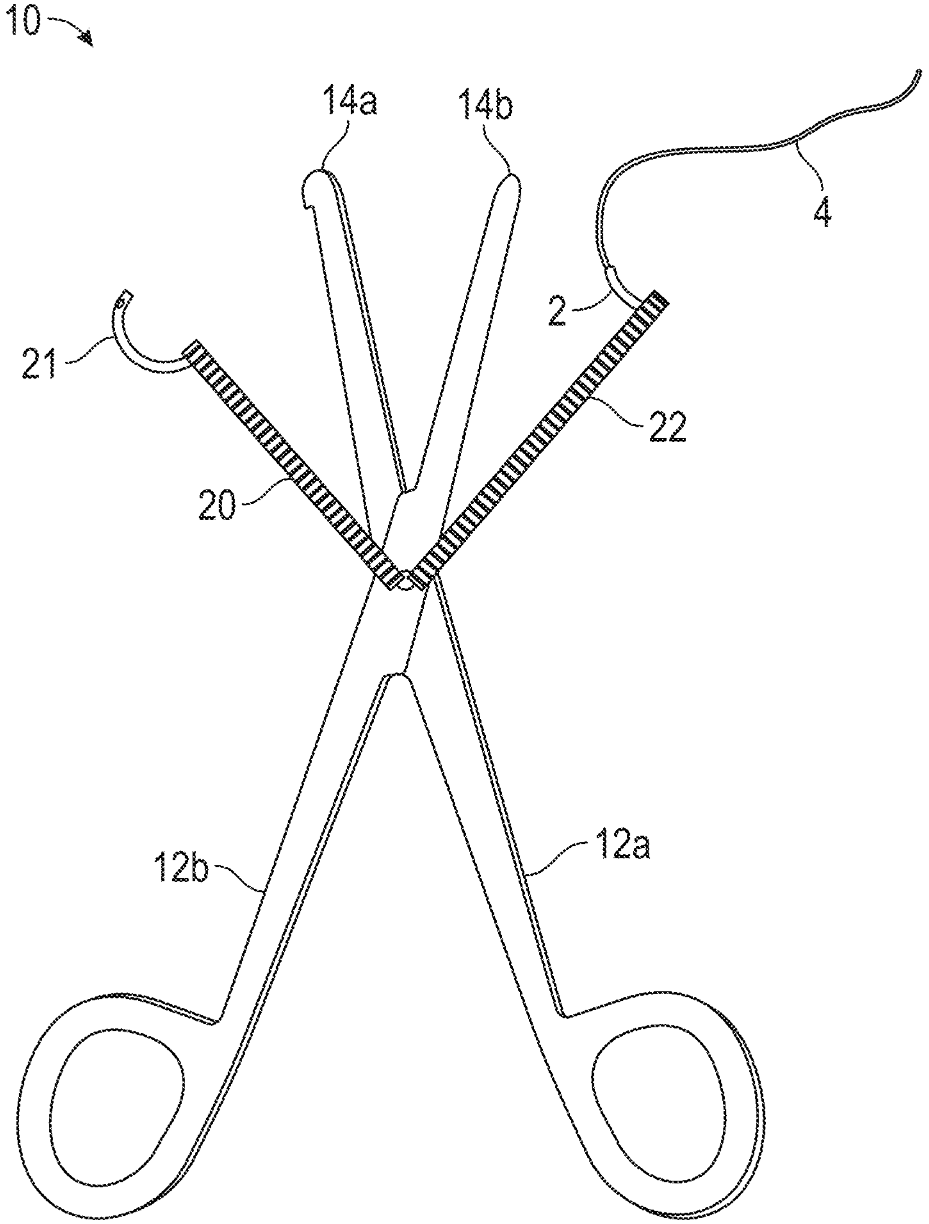
FIG. 5E is a top view of the suturing forceps of FIG. 5A in a different position in accordance with the present disclosure.
Figure 5F:
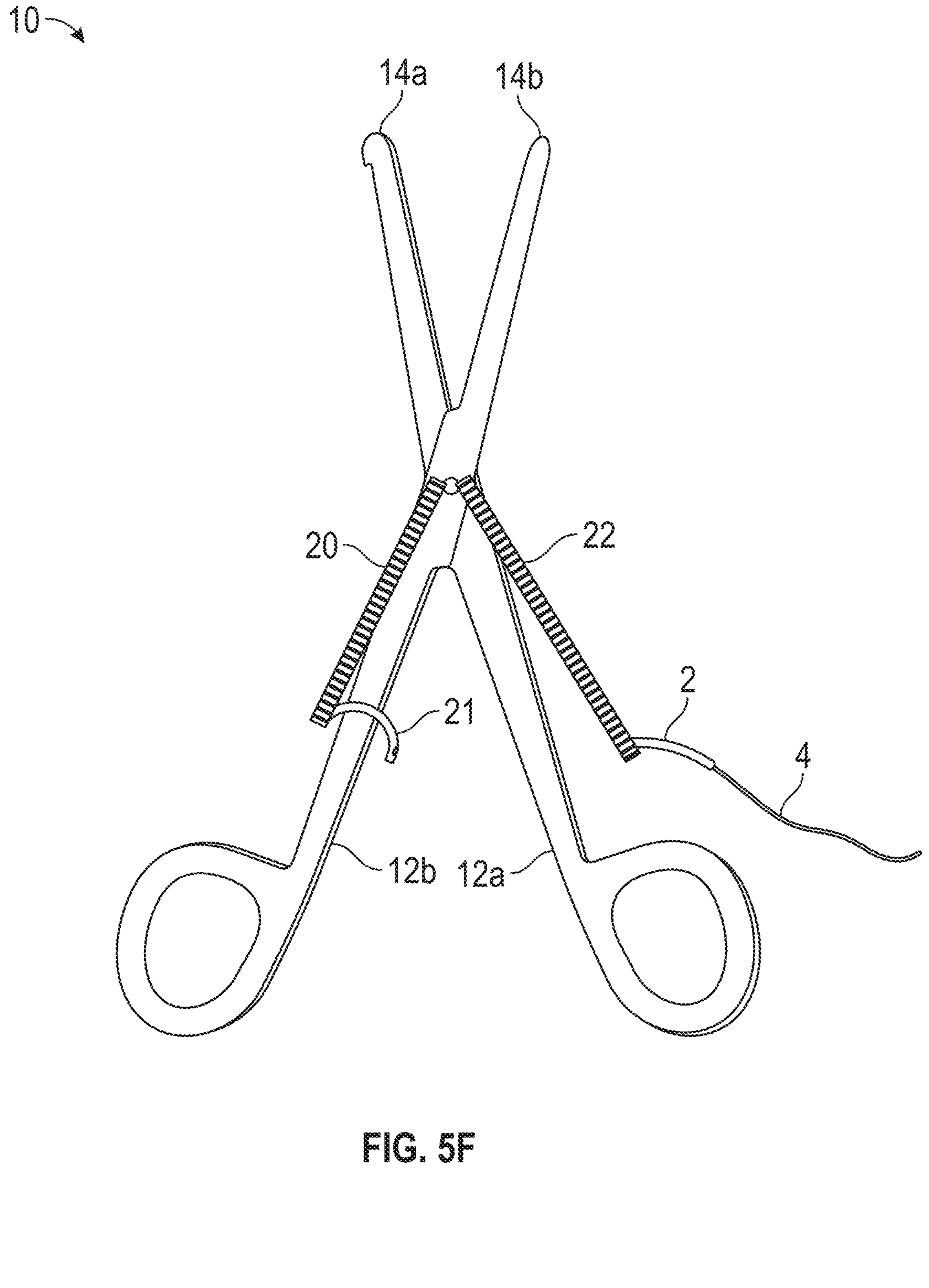
FIG. 5F is a top view of the suturing forceps of FIG. 5A in a different position in accordance with the present disclosure.
Figure 5G:
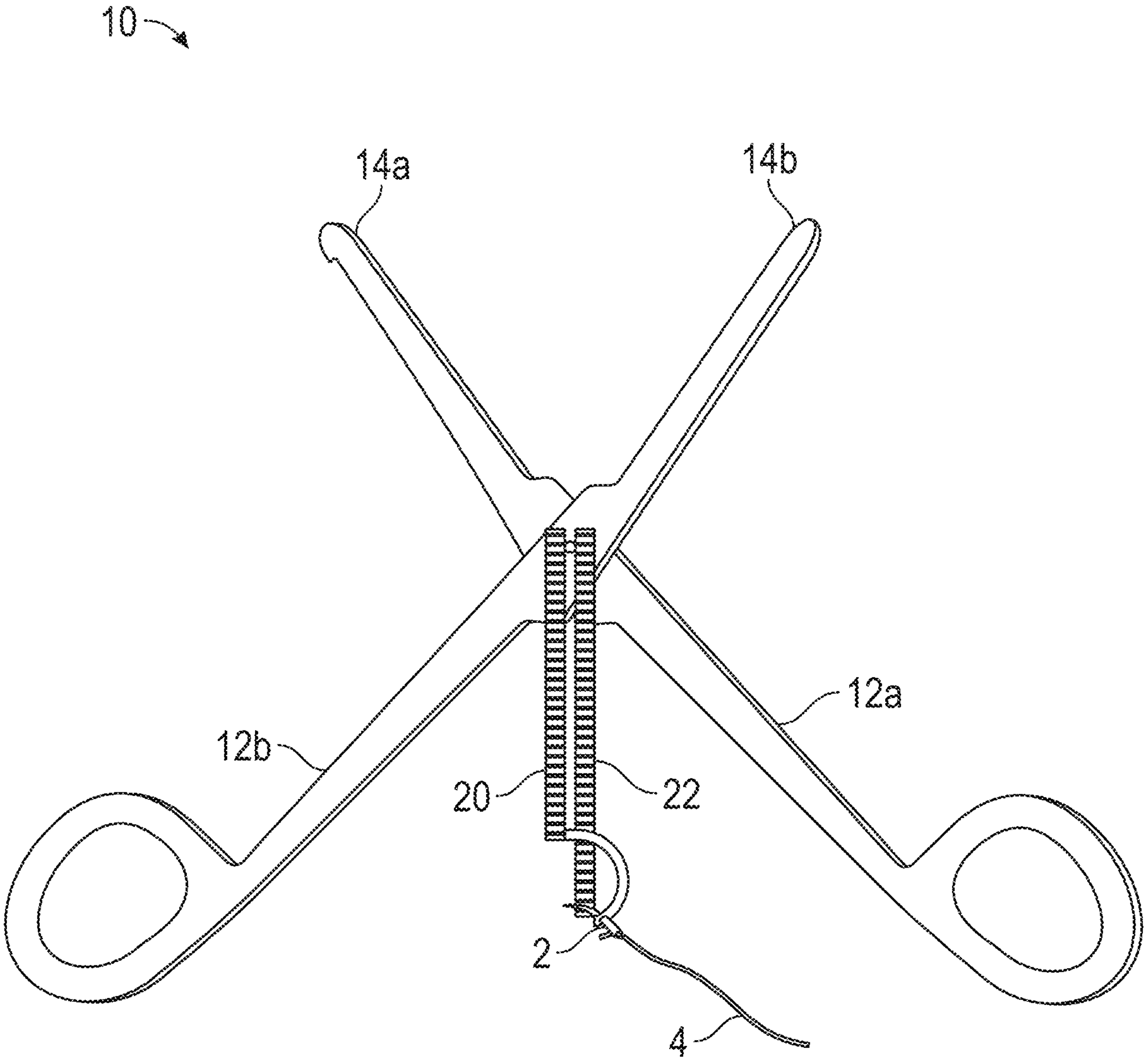
FIG. 5G is a top view of the suturing forceps of FIG. 5A in a different position in accordance with the present disclosure.

Referring to FIGS. 5A-5G, an exemplary suturing forceps 10 embodiment is shown to illustrate the movement of the extension 21 in accordance with the present disclosure. For the sake of simplicity, no gear mechanism is shown in FIGS. 5A-5G. FIG. 5A shows the needle 2 held by the extension 21 that is being transferred from the return arm 22. FIG. 5B shows the extension 21 rotating backward with the needle 2 and the arms 20, 22 moving towards the grip ends 14*a*, 14*b* side of the forceps 10. FIG. 5C shows the extension 21 rotating forward in preparation for the suturing. FIG. 5D shows the needle 2 pushed forward through the flesh and into the pads of return arm 22. FIG. 5E shows the pads holding the end of the needle 2 and the arms 20, 22 arms moving back to the starting position. FIG. 5F show the extension 21 rotating back to get ready to grip the needle 2 from the back. FIG. 5G is like the position shown in FIG. 5A, completing the cycle with the extension 21 grabbing the back of the needle 2 ready to repeat the operation. The extension 21 is a different way to make sure the suture needle 2 and thread 4 is repositioned for the next cycle by coming from behind the return arm 22 and grasping the needle 2 in the same way as illustrated in FIG. 5A to repeat the cycle for as many stitches as the user desires. A cam can be used to a channel cut that is slightly higher or lower on the backside of the circular gear to move the arm extension 21 to the desired position. The arm extension 21 could be configured to pivot with a sliding piece connected to the cam and channel.

The arm extension 21 can be sized, shaped and configured for different suture applications. For example, for thin tissue the arm extension 21 could be arranged substantially flat so the needle 4 is introduced in straight one side and out the other. For larger tissue, such as flat and thicker like skin/muscle, the curve of the arm extension 21 may be configured to come in at an angle and use the curve to exit opposite side of the incision at a desired angle so that the user can pull the suture needle 2 out and start again. In some embodiments, the angle of the swing of the arm extension 21 is adjustable.

Advantageously, the pressure disclosure provides suturing forceps and methods of suturing that provide for consistent speed and depth of suture stitches installation with a convenient and ergonomical device. The suturing forceps of the present disclosure can operate with standard sutures from existing manufacturers. In some embodiments, the suturing forceps include one or more magnets on the suture arm and/or the return arm and can operate with a magnetic suture. There are many types of sutures and suture needles.

Some needles are curved and some needles are straight. For example and without limitation, the suturing forceps of the present disclosure may be compatible with 3/8 curved style sutures, but other suture types and sizes are within the scope of the present disclosure.

Figure 6A:
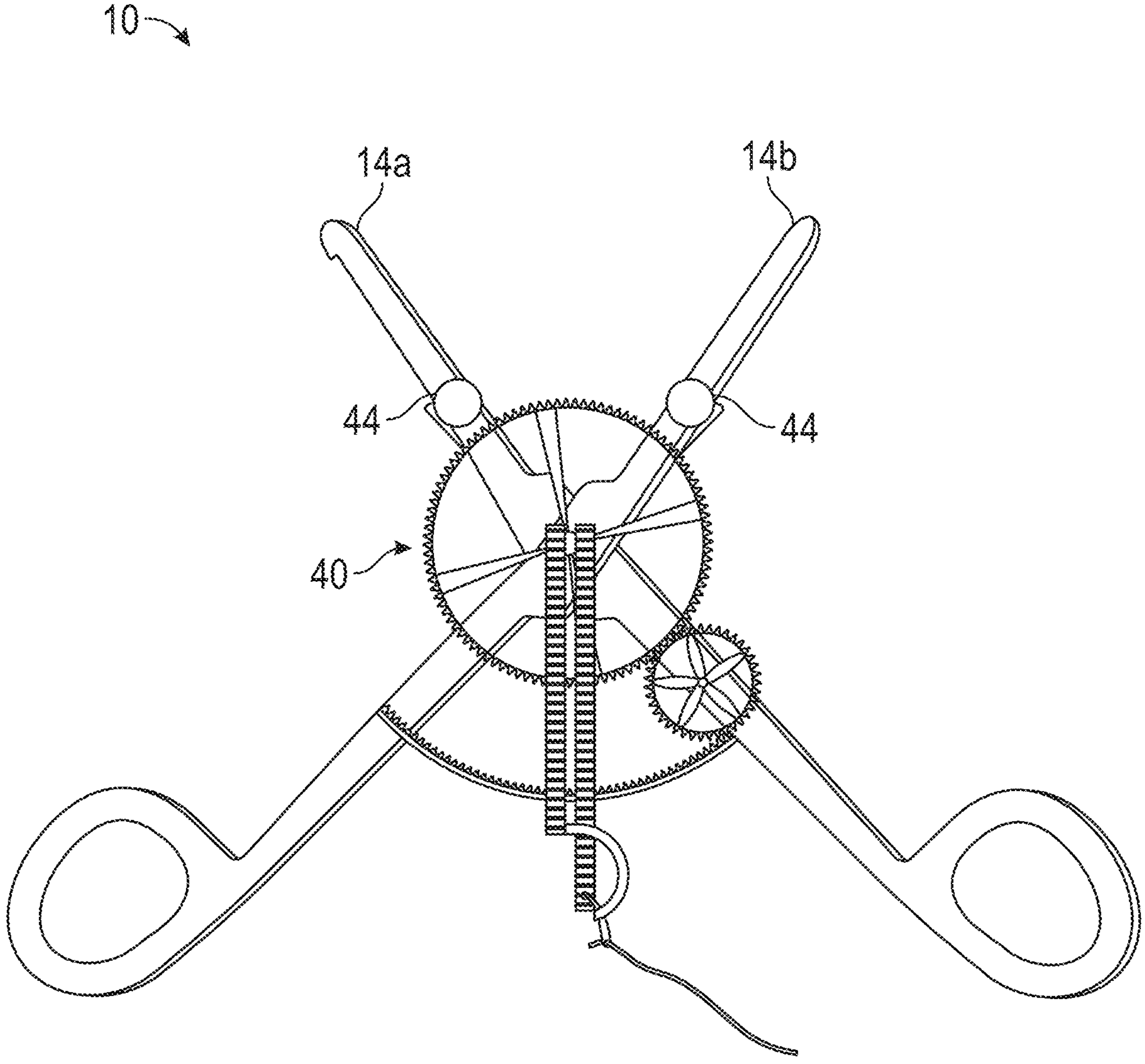
FIG. 6A is a top view of a suturing forceps having flexible connections between a gear mechanism and grip ends in accordance with the present disclosure.
Figure 6B:
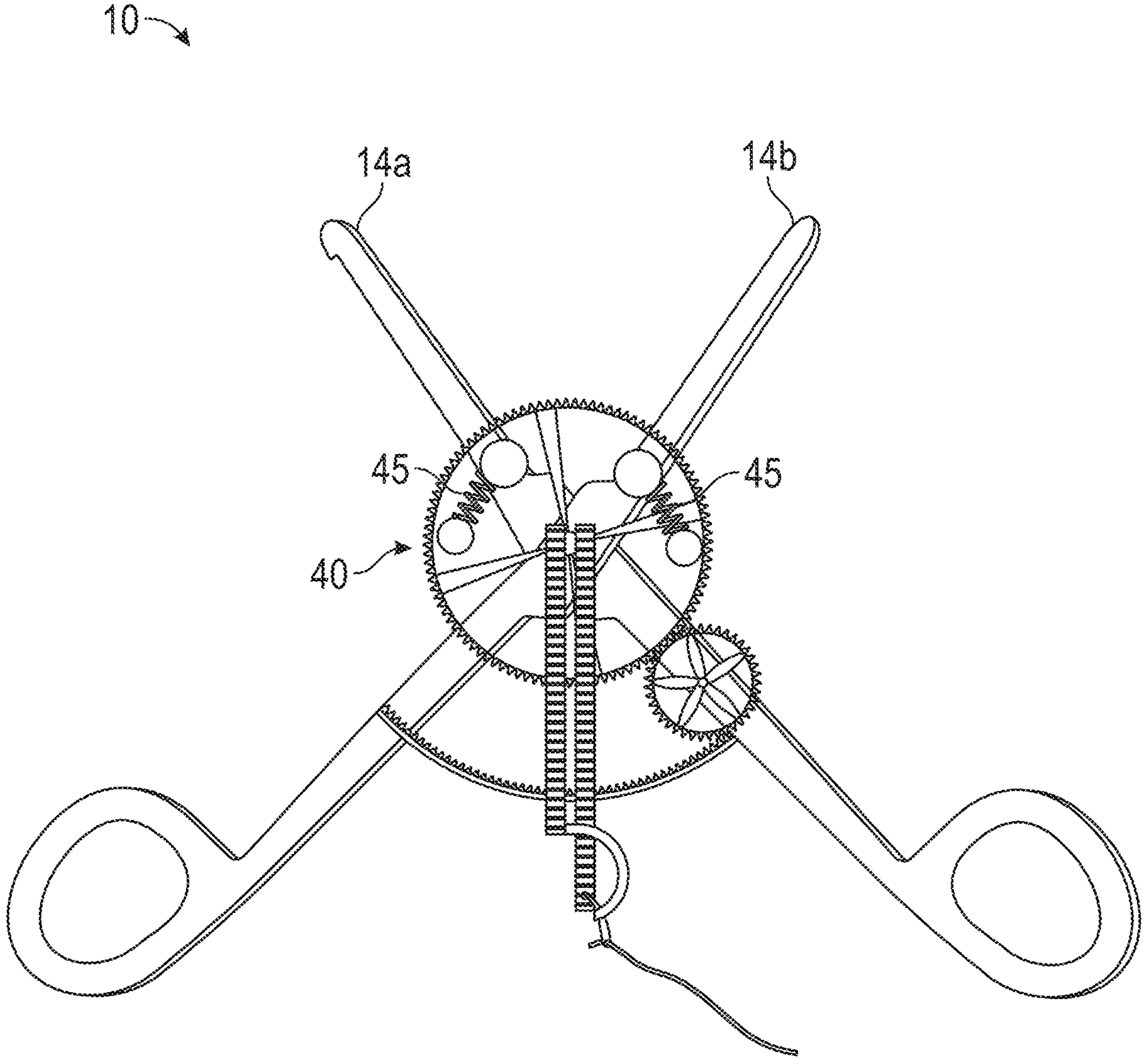
FIG. 6B is a top view of a suturing forceps having spring connections between a gear mechanism and grip ends in accordance with the present disclosure.

The arms 20, 22 of the forceps 10 of the present disclosure can be configured to move in a variety of manners with respect to the tool arms 12*a*, 12*b*. For example and without limitation, the arms 20, 22 could be synchronized (e.g. via gearing) so that the grip ends 14*a*, 14*b* close the moment before the needle 2 is pushed through the tissue of the patient. Alternatively, the grip ends 14*a*, 14*b* connected with flexible connections 44 (FIG. 6A) or spring connections 45 (FIG. 6B) that allow for the grip ends 14*a*, 14*b* to hold the flesh of the patient in place with increasing pressure at the point where the needle 2 passes through and hold the flesh in place while the needle 2 is in motion. A relative position of where the suture arm 20 and the return arm 22 reach the closed position relative to where the first grip end 14*a* and the second grip end 14*b* reach a clamped position is adjustable. In other words, a user can adjust the gear mechanism 40 or other mechanism to change when or where the suture arm 20 reaches the closed position (or other point) to force the needle 2 into the flesh of the patient with respect to when the grip ends 14*a*, 14*b* come together to clamp the flesh in place. For example, a nut or knob can be arranged to advance or retreat the gearing of the differential mechanism 40 such that the suture arm 20 and return arm 22 reach the closed position at the desired time or relative position of the grip ends 14*a*, 14*b* and/or the proximal ends of the tool arms 12*a*, 12*b*.

The foregoing description of embodiments of the present invention has been presented for the purpose of illustration and description. It is not intended to be exhaustive or to limit the invention to the form disclosed. Obvious modifications and variations are possible in light of the present disclosure. The embodiments described were chosen to best illustrate the principles of the invention and practical applications thereof to enable one of skill in the art to utilize the invention in various embodiments and with various modifications as suited to the particular use contemplated.

What is claimed is:

1. Suturing forceps comprising:

a first tool arm connected to a second tool arm, each configured to rotate about a pivot;

a first grip end arranged at a distal end of the first tool arm and a second grip end arranged at a distal end of the second tool arm;

a suture arm connected to the first tool arm and/or the second tool arm through a differential rotation mechanism;

wherein the suture arm is configured to retain a suture needle; and wherein the differential rotation mechanism is configured such that rotation of the first tool arm and/or the second tool arm causes the differential rotation mechanism to cause the suture arm to rotate.

2. The suturing forceps according to claim 1, wherein the differential rotation mechanism comprises a gear mechanism.

3. The suturing forceps according to claim 1, wherein the differential rotation mechanism is configured such that a rotational degree of the rotation of the first tool arm and/or the second tool arm causes the suture arm to rotate through a larger rotational degree than the rotational degree of the rotation of the first tool arm and/or the second tool arm.

4. The suturing forceps according to claim 1, further comprising:

a return arm connected to the first tool arm and/or the second tool arm through the differential rotation mechanism;

wherein the return arm is configured to retain the suture needle; and wherein rotation of the first tool arm and/or the second tool arm causes the differential rotation mechanism to cause the return arm to rotate.

5. The suturing forceps according to claim 4, wherein the differential rotation mechanism is configured such that a rotational degree of the rotation of the first tool arm and/or the second tool arm causes the return arm to rotate through a larger rotational degree than the rotational degree of the rotation of the first tool arm and/or the second tool arm.

6. The suturing forceps according to claim 5, wherein the differential rotation mechanism is configured to cause the suture arm and the return arm to move to a closed position when a user moves handle ends of the first tool arm and the second tool arm towards each other.

7. The suturing forceps according to claim 6, wherein when the suture arm and the return arm are in the closed position, the first grip end and the second grip end are in a clamping state, and wherein the first grip end and the second grip end are configured to clamp tissue when in the clamping state.

8. The suturing forceps according to claim 1, wherein a first finger ring is arranged at a proximal end of the first tool arm and a second finger ring is arranged at a proximal end of the second tool arm.

* * * * *